United States Patent [19]

Binderup

[11] Patent Number: 5,376,651
[45] Date of Patent: Dec. 27, 1994

[54] USE OF 20(R)-22-OXA-VITAMIN D ANALOGUES FOR THE TREATMENT OF SKIN AGEING

[75] Inventor: Lise Binderup, Taastrup, Denmark

[73] Assignee: Leo Pharmaceutical Products Ltd. A/S (Lovens Kemiske Fabrik Produktionsaktiesel SKAB), Ballerup, Denmark

[21] Appl. No.: 956,504

[22] PCT Filed: Jun. 24, 1991

[86] PCT No.: PCT/DK91/00172

§ 371 Date: Jan. 11, 1993

§ 102(e) Date: Jan. 11, 1993

[87] PCT Pub. No.: WO92/01454

PCT Pub. Date: Feb. 6, 1992

[30] Foreign Application Priority Data

Jul. 18, 1990 [GB] United Kingdom ............... 9015774

[51] Int. Cl.$^5$ .......................... A61K 31/59; C07J 9/00
[52] U.S. Cl. ........................ 514/167; 514/35; 514/410
[58] Field of Search .............. 514/410, 35, 167, 168

[56] References Cited

U.S. PATENT DOCUMENTS

| | | | |
|---|---|---|---|
| 4,866,048 | 9/1989 | Calverley et al. | 514/167 |
| 5,098,899 | 3/1992 | Gilbert et al. | 514/167 |
| 5,190,935 | 3/1993 | Binderup et al. | 514/167 |
| 5,206,229 | 4/1993 | Calverley et al. | 514/167 |
| 5,254,538 | 10/1993 | Holick et al. | 514/35 |

OTHER PUBLICATIONS

WO, A, 90099991 (Sep. 1990.).
T. Okano et al, "Vitamin D Molecular, Cellular and Clinical Endocrinology", Proceedings of the Seventh Workshop on Vitamin D, Apr. 1988, pp. 462–463.
S. Morimoto et al, "Comparison of the Inhibitions of Proliferation of Normal and Psoriatic Fibroblasts by Lalpha, 25–dihydroxyvitamin D3 and Synthetic Analigues of Vitamin De with an Oxygen Atom in their side chain":, Biochemistry International, vol. 19, No. 5, Nov. 1989, pp. 1143–1144.
T. Valaja et al, "Affinity of 22-oxa-1,25(OH)2D3 for 1,25-dihydroxyvitamin D receptor and its effects on the Synthesis of Osteoclacin in Human Osterosarcoma Cells", Biochemical and Biophysical Research Communications, Vil 169, No. 2, Jun. 1990, pp. 629–635.
Patent Abstract of Japan, vol. 12, No. 462 (c-549) [3309] Dec. 1988=JP 63-183534 (Jul. 1988).
Patent Abstract of Japan, vol. 12, No. 349 (C-529) [3196] Sep. 1988,=JP 63-107930 (May 1988).
T. Oikawa et al, "Inhibition of Angiogenesis by Vitamin D3 Analogues", European Journal of Pharmacology, vol. 178, No. 2, Jan. 1990, pp. 257–250.

*Primary Examiner*—Arthur C. Prescott
*Attorney, Agent, or Firm*—Cushman, Darby & Cushman

[57] ABSTRACT

The present invention relates to the use of 20(R)-22-oxavitamin D analogues for treatment or prevention of skin ageing, and to the use of such compounds for preparation of pharmaceutical compositions for teatment and/or prevention of skin ageing.

6 Claims, 2 Drawing Sheets

USE OF 20(R)-22-OXA-VITAMIN D ANALOGUES FOR THE TREATMENT OF SKIN AGEING

This invention relates to the use of 20(R)-22-oxavitamin D analogues for treatment or prevention of skin ageing, and to the use of such compounds for preparation of pharmaceutical compositions for treatment and/or prevention of skin ageing.

Ageing of the skin involves the intrinsic process of senescense and extrinsic damage induced by chronic exposure to UV radiation (photoageing).

Clinically, the ageing process is characterized by skin changes such as thinning, loss of elasticity and wrinkling. The main histologic features of aged skin include epidermal athrophy and dysplasia as well as dermal damage with marked elastosis and loss of collagen.

It has recently been demonstrated that topical tretinoin can improve the features of photodamaged skin by daily continuous application (1). However, because of the irritant properties of tretinoin the use of this drug is associated with unpleasant side effects, and therefore there is a need for better tolerated and more active products for prevention and reversal of skin ageing.
(1) Weiss, J. S. et al, JAMA, 259(1988), 527-32.

We have now found that certain analogues of vitamin D are active in the prevention and treatment of skin ageing and at the same time are free of the irritant effects characteristic of retinoids.

It is well known that a number of vitamin D metabolites and analogues inhibit the proliferation of keratinocytes (2)(3)(4). As a result of this, a thinning of the epidermal layer is seen in guinea pigs in areas treated with a petrolatum ointment containing such an analogue compared to areas treated with petrolatum alone (4). A similar reduction of epidermal thickness is seen in psoriatic lesions treated with 1,25-dihydroxyvitamin $D_3$ (3).
(2) Kuroki, T. et al, Ann. N.Y. Acad. Sci. (1988) 548, 45-55.
(3) Holick, M. F. , Proc. Exp. Biol. Med., 191 (1989), 246
Kato, T. et al, Br. J. Dermatol., 117 (1987), 528-30

However, in contrast to this, we have now surprisingly seen a profound thickening of epidermis in rats treated with an ointment containing a member of a series of new 20(R)-22-oxa-vitamin D analogues e.g. those described in our copending international application PCT/DK90/00036, indicating the usefulness of such preparations for treatment or profylaxis of skin ageing, including photo-ageing.

The compounds described in PCT/DK90/00036 are represented by the general formula I

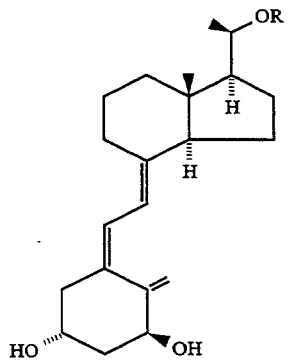

in which formula R stands for an alkyl group containing from 4 to 12 carbon atoms optionally substituted with a hydroxy group.

Preferably R is a group of formula II

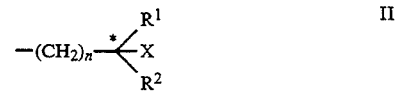

where n is an integer from 1 to 7; $R^1$ and $R^2$, which may be the same or different, stand for hydrogen, lower alkyl, lower cycloalkyl, or, taken together with the carbon atom (starred in formula II) bearing the group X, $R^1$ and $R^2$ can form a $C_3$-$C_8$ carbocyclic ring; X stands for hydrogen or hydroxy.

In the context of this invention, the expression "lower alkyl" indicates a straight or branched saturated or unsaturated carbon chain containing from 1 to 5 carbon atoms, and the expression "lower cyclo-alkyl" indicates a saturated or unsaturated $C_3$-$C_7$ carbocyclic ring.

As can be seen from formula I and II, depending on the meanings of R, X, $R^1$ and $R^2$, the compounds of the invention can comprise several diastereoisomeric forms (e.g. R or S configuration at the starred carbon atom). The invention covers all these diastereoisomers in pure form and also mixtures of diastereoisomers.

Among compounds of particular interest are the compounds of formula I in which n (in formula II) is 3 or 4 and $R^1$ and $R^2$ represent methyl, ethyl or n-propyl groups.

Most preferred are the compounds in which n is 3 or 4 and $R^1$ and $R^2$ represents ethyl groups.

The compounds are formulated in pharmaceutical compositions which are suitable for topical treatment, and in which the active ingredient comprises from 0.01 ppm to 10 ppm.

The formulations include liquid or semi-liquid preparations such as liniments, lotions, applicants, oil-in-water or water-in-oil emulsions such a creams, ointments or pastes.

In addition to the pharmaceutical carrier the formulations may include one or more additional ingredients such as diluents, buffers, flavouring agents, binders, surface active agents, thickeners, lubricants, preservatives, e.g. methyl hydroxybenzoate (including anti-oxidants), emulsifying agents and the like.

The compositions may further contain other therapeutically active compounds usually applied in the treatment of skin ageing.

The present invention further concerns a method for prevention of skin ageing or for treating patients already suffering from skin ageing, said method consisting of administering to a patient in need of treatment an effective amount of one or more compounds of formula I, alone or in combination with one or more other therapeutically active compounds usually applied in the treatment of skin ageing. The treatment with the present compounds and/or with further therapeutically active compounds may be simultaneous or with intervals.

EXAMPLE 1

Cream

| | |
|---|---|
| 1(S),3(R)-Dihydroxy-20(R)-(4'-hydroxy-4'-methyl-1'-pentyloxy)-9,10-seco-pregna-5(Z),7(E),10(19)-triene | 5 mg |

-continued

| Cream | |
|---|---|
| (active substance) | |
| Cetomacrogol 1000 | 30 g |
| Cetostearyl alcohol | 60 g |
| Chloroallylhexaminium chloride | 0.5 g |
| Propylenglycol | 30 g |
| Disodium hydrogenphosphate | 2 g |
| Sodium dihydrogenphosphate | 0.1 g |
| Liquid paraffin | 50 g |
| White petrolatum | 170 g |
| Purified water | up to 1000 g |

Melt cetomacrogol 1000, cetostearyl alcohol, liquid paraffin and white petrolatum at 75° C. Dissolve propylenglycol in water at 75° C. and mix the solution with the fatty phase. Homogenize the emulsion and cool to 30° C. Mill the active compound to particle size below 5 μm and suspend in an aqueous solution of disodium hydrogenphosphate, sodium dihydrogenphosphate and chloroallylhexaminium chloride. Add the suspension to the emulsion and fill the cream in tubes.

EXAMPLE 2

| Ointment | |
|---|---|
| 1(S),3(R)-Dihydroxy-20(R)-(4'-hydroxy-4'-ethyl-1'-hexyloxy)-9,10-seco-pregna-5(Z),7(E),10(19)-triene (active substance) | 1 mg |
| Disodium hydrogen phosphate | 0.5 g |
| Polyoxyethylene(2)stearyl alcohol | 60 g |
| Propylene glycol | 150 g |
| Purified water | 50 g |
| White petrolatum | 740 g |

Dissolve disodiumhydrogenphosphate and the active substance in a mixture of propylene glycol and water. Melt the white petrolatum and add the propylene glycol solution. Homogenize and cool the ointment during agitation. Fill the ointment into tubes.

EXAMPLE 3

| Lotion | |
|---|---|
| 1(S),3(R)-Dihydroxy-20(R)-(5'-hydroxy-5'-ethyl-1'-heptyloxy)-9,10-seco-pregna-5(Z),7(E),10(19)-triene (active substance) | 2 mg |
| Absolute alcohol | 400 g |
| Hydroxypropylcellulose | 1 g |
| Menthol | 1 g |
| Sodium citrate | 1 g |
| Propylenglycol | 40 g |
| Purified water | up to 1000 ml |

Dissolve hydroxypropylcellulose, sodium citrate and propylenglycol in water. Mix with a solution of the active substance and menthol in absolute alcohol. Fill the lotion in polyethylen plastic bottles.

EXAMPLE 4

| Cream | |
|---|---|
| 1(S),3(R)-Dihydroxy-20(R)-(5'-hydroxy-5'-methyl-1'-hexyloxy)-9,10-seco-pregna-5(Z),7(E),10(19)-triene (active substance) | 5 mg |
| Cetomacrogol 1000 | 30 g |
| Cetostearyl alcohol | 60 g |
| Chloroallylhexaminium chloride | 0.5 g |

| Cream | |
|---|---|
| Propylenglycol | 30 g |
| Disodium hydrogenphosphate | 2 g |
| Sodium dihydrogenphosphate | 0.1 g |
| Liquid paraffin | 50 g |
| White petrolatum | 170 g |
| Purified water | up to 1000 g |

Melt cetomacrogol 1000, cetostearyl alcohol, liquid paraffin and white petrolatum at 75° C. Dissolve propylenglycol in water at 75° C. and mix the solution with the fatty phase. Homogenize the emulsion and cool to 30° C. Mill the active compound to particle size below 5 μm and suspend in an aqueous solution of disodium hydrogenphosphate, sodium dihydrogenphosphate and chloroallylhexaminium chloride. Add the suspension to the emulsion and fill the cream in tubes.

EXAMPLE 5

Effects of 1(S),3(R)-Dihydroxy-20(R)-(4'-hydroxy-4'-ethyl-1'-hexyloxy)-9,10-seco-pregna-5(Z),7(E),10(19)-triene (KH 1060) on epidermal thickness in rats The vitamin D analogue KH 1060 was formulated in a petrolatum ointment (containing 10% propylene glycol) at 5 μg/g ointment. The ointment was applied to the back of 5 Spraque-Dawley rats, 0.5 g per kg body weight, once daily for 4 weeks. Two other groups of 5 rats similarly received treatment with placebo ointment or ointment containing 1,25-dihydroxycholecalciferol (1,25(OH)$_2$D$_3$, 20 μg/g ointment). The administered dosage was thus 2.5 μg/kg body weight/day for KH 1060 and 10 μg/kg body weight/day for 1,25(OH)$_2$D$_3$.

At the end of treatment all animals were sacrificed by exsanguination and skin samples were removed for histopathological examination. The tissue was embedded in paraffin, sections of 4–5 mm were prepared and stained with hematoxylin and eosin. Microphotographs were taken at 100× magnification.

Figure 1:
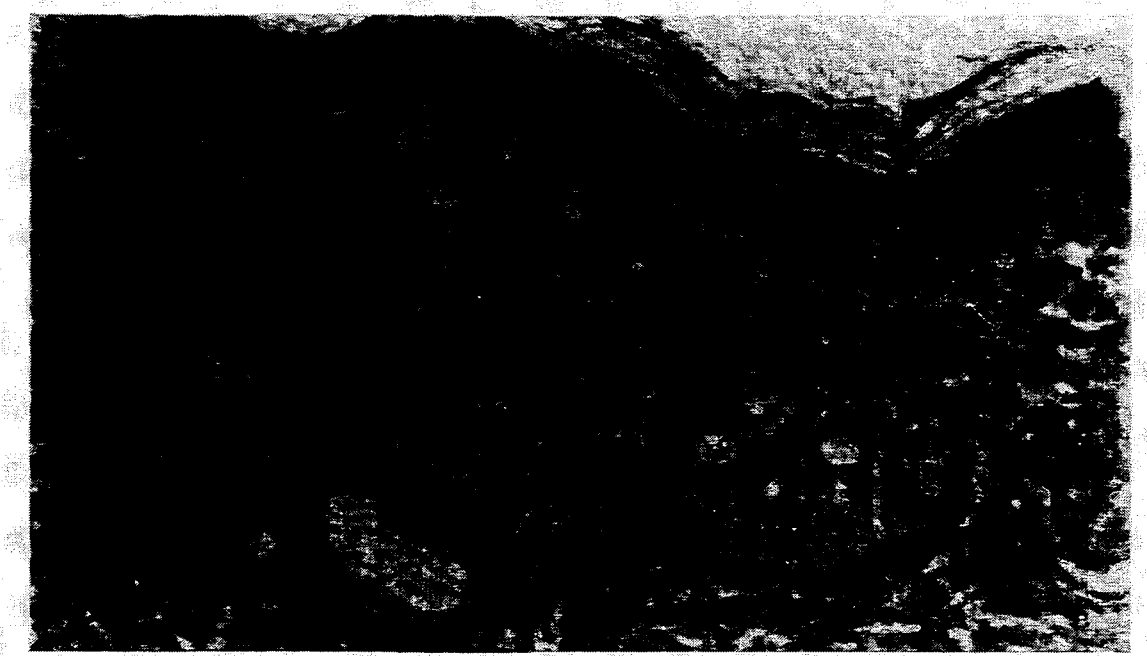
FIG. 1. shows a section from the skin of rats treated with placebo ointment. A thin layer of epidermis is clearly visible at the left side of the section.
Figure 2:
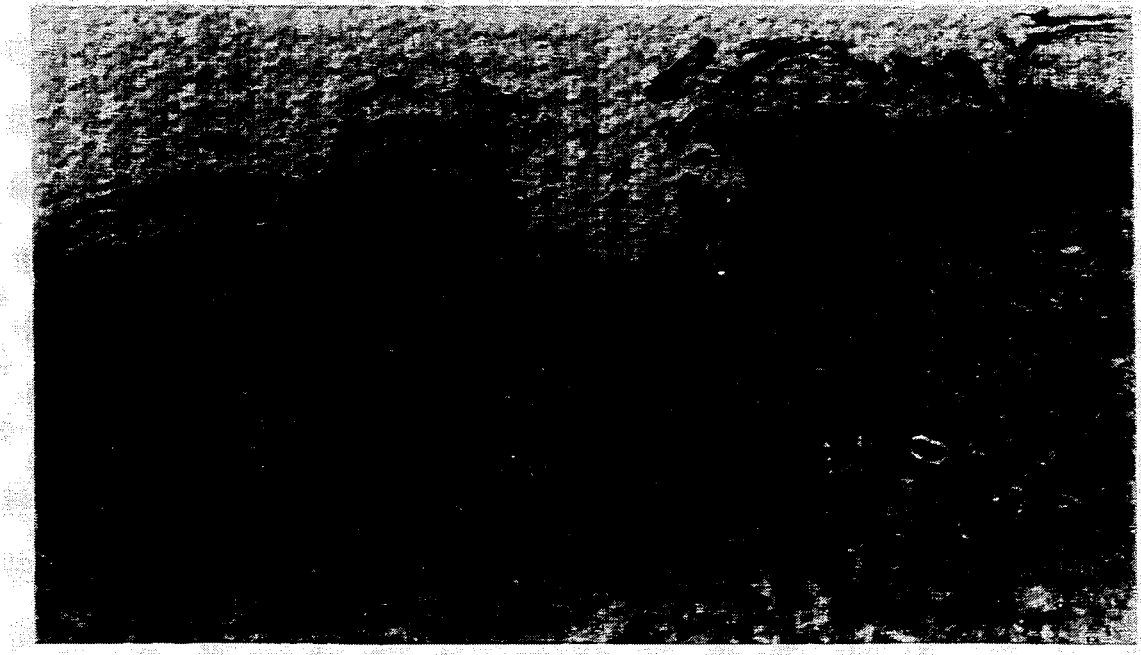
FIG. 2 shows a section from the skin of rats treated with 1,25(OH)$_2$D$_3$ ointment at 10 μg/kg/day. The thickness of the epidermal layer is similar to that seen in the rats treated with placebo ointment.
Figure 3:
FIG. 3 shows a section from the skin of rats treated with KH 1060 ointment at 2.5 μg/kg/day. A very striking thickening of the epidermal layer is seen (approx. 3 times the thickness of the skin from placebo treated rats). These changes were observed in all 5 rats treatment with KH 1060 ointment. No changes indicative of inflammatory processes were seen in the underlying dermal layers.

What we claim is:

1. A method of treating skin ageing which comprises administering to the skin an effective amount of 20(R)-22-oxavitamin D analogue of the formula I

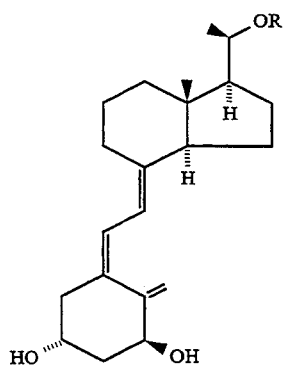

in which formula R stands for an alkyl group containing from 4 to 12 carbon atoms optionally substituted with a hydroxy group.

2. The method use according to claim 1, in which R in the active component is a group of formula II

where n is an integer from 1 to 7; $R^1$ and $R^2$, which may be the same or different, stand for hydrogen, a straight or branched saturated or unsaturated carbon chain containing from 1 to 5 carbon atoms, a saturated or unsaturated $C_3$–$C_7$ carbocyclic ring, or, taken together with the carbon atom (starred in formula II) bearing the group X, $R^1$ and $R^2$ can form a $C_3$–$C_8$ carbocyclic ring; X stands for hydrogen or hydroxy.

3. The method according to claim 2, in which n is 3 or 4 and $R^1$ and $R^2$ represent methyl, ethyl or n-propyl groups.

4. The method according to claim 2, in which n is 3 or 4 and $R^1$ and $R^2$ represent ethyl groups.

5. The method according to claim 1, in which the active component is 1(S),3(R)-dihydroxy-20(R)-(5′-hydroxy-5′-methyl-1-hexyloxy)-9,10-seco-pregna-5(Z),7(E),10(19)-triene.

6. The method according to claim 1, in which the active component is 1(S),3(R)-dihydroxy-20(R)-(4′-hydroxy-4′-ethyl-1′-hexyloxy)-9,10-seco-pregna-5(Z),7(E),10(19)-triene.

* * * * *